(12) United States Patent
Tanaka et al.

(10) Patent No.: US 9,808,150 B2
(45) Date of Patent: Nov. 7, 2017

(54) IMAGE PROCESSING APPARATUS, CONTROL METHOD THEREFOR, AND STORAGE MEDIUM STORING PROGRAM

(71) Applicant: CANON KABUSHIKI KAISHA, Tokyo (JP)

(72) Inventors: Tatsuya Tanaka, Higashimurayama (JP); Keisuke Oyaizu, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/184,816

(22) Filed: Jun. 16, 2016

(65) Prior Publication Data
US 2016/0374547 A1    Dec. 29, 2016

(30) Foreign Application Priority Data
Jun. 23, 2015   (JP) .................................. 2015-126044

(51) Int. Cl.
| | | |
|---|---|---|
| *A61B 3/14* | (2006.01) | |
| *A61B 3/00* | (2006.01) | |
| *A61B 3/10* | (2006.01) | |
| *A61B 3/12* | (2006.01) | |

(52) U.S. Cl.
CPC .......... *A61B 3/0025* (2013.01); *A61B 3/0058* (2013.01); *A61B 3/102* (2013.01); *A61B 3/1225* (2013.01); *A61B 3/14* (2013.01)

(58) Field of Classification Search
CPC ......... A61B 3/0025; A61B 3/102; A61B 3/14; A61B 3/0058; A61B 3/1225
USPC .................................................. 351/206, 246
See application file for complete search history.

(56) References Cited

FOREIGN PATENT DOCUMENTS

JP          2014-014727 A        1/2014

*Primary Examiner* — Jack Dinh
(74) *Attorney, Agent, or Firm* — Canon U.S.A., Inc. IP Division

(57) ABSTRACT

An image processing apparatus includes: a tomographic image acquisition unit that acquires a first tomographic image of a subject's eye captured at a first time point that is a past time point; a tomographic image capturing unit that acquires a second tomographic image of the subject's eye captured at a second time point later than the first time point; and an image display control unit that, if one image capturing region of an image capturing region of the first tomographic image and an image capturing region of the second tomographic image is larger than the other image capturing region, performs control to provide, on an image display portion, a display of both a tomographic image of only a partial region of the one image capturing region which is a corresponding region corresponding to the other image capturing region and a tomographic image of the other image capturing region.

13 Claims, 5 Drawing Sheets

IMAGE PROCESSING APPARATUS, CONTROL METHOD THEREFOR, AND STORAGE MEDIUM STORING PROGRAM

BACKGROUND OF THE INVENTION

Field of the Invention

The present invention relates to an image processing apparatus that processes an image obtained by performing imaging of a subject's eye, a control method therefor, and a storage medium storing a program that causes a computer to execute the control method.

Description of the Related Art

In diagnostic imaging in ophthalmology as an example, recent use of a tomographic image in addition to an eye fundus image that has been widely used allows three-dimensional observation of an internal state of a retinal layer of an eye of a subject (subject's eye). Thus, a diagnosis made by using a tomographic image is expected to be useful for making a more accurate diagnosis of a disease.

The above-described eye fundus image is captured by using a fundus camera, scanning laser ophthalmoscope (SLO), or infrared (IR) rays, for example. The above-described tomographic image is captured by using an optical coherence tomography (OCT) instrument, for example.

In recent years, there have been provided apparatuses that enable follow-up observation of the internal state of the retinal layer of a subject's eye by using the above OCT instrument, thus enabling observation of the development of a disease or the postoperative clinical course. In follow-up observation of a subject's eye, a newly acquired tomographic image is compared with a tomographic image of the same site acquired in the past. This comparison between the images is typically made by displaying the newly acquired tomographic image and the tomographic image acquired in the past simultaneously (hereinafter referred to as "follow-up display"). This follow-up display facilitates a comparative understanding of corresponding portions from two tomographic images and is very useful for follow-up observation.

With improvements in technology, it has become possible for an OCT apparatus that captures a tomographic image to capture a tomographic image of a wider region in a single imaging session. There are also facilities having a plurality of OCT apparatuses with different imaging performance (for example, the size of an image capturing region whose image can be captured). For example, in Japanese Patent Laid-Open No. 2014-14727, a technique is proposed in which, in the case where a region whose image can be captured is enlarged as a result of the improved performance of a tomographic image capturing apparatus, imaging conditions for a tomographic image to be captured for follow-up observation are set.

In the case where follow-up observation of a subject's eye is carried out, a follow-up display is most often used as described above. For example, in the case of a facility having a plurality of OCT apparatuses with different sizes (dimensions) of image capturing regions, there is a situation in which a captured tomographic image whose image capturing region is different in size from that of a tomographic image captured in the past has to be used in follow-up observation of an eye of a subject. In this case, when an attempt to display all image regions of each tomographic image within a predetermined follow-up display range is made, one tomographic image is reduced or enlarged in size to be displayed because the sizes of the respective image capturing regions are different. In this case, since two tomographic images have a different display scaling factor, for example, the thicknesses of cross sections of the subject's eye may not be accurately compared with each other, raising a concern that this may make effective follow-up observation difficult.

Thus, it is considered that the entirety of each tomographic image is displayed at an original scaling factor on a follow-up display screen. In this case, however, the tomographic image whose image capturing region is large (wide) contains an image region not used for comparison, thereby making a comparative understanding of corresponding portions between the tomographic images difficult and increasing the burden of follow-up observation on an examiner. In this regard, the technique disclosed in Japanese Patent Laid-Open No. 2014-14727 is a technique of simply setting imaging conditions for the case where a tomographic image whose image capturing region is enlarged with respect to a past tomographic image is captured, and thus it is difficult to solve this issue.

SUMMARY OF THE INVENTION

An image processing apparatus according to the present invention includes: a first tomographic image acquisition unit configured to acquire a first tomographic image of a subject's eye captured at a first time point that is a past time point; a first image capturing region acquisition unit configured to acquire a first image capturing region that is an image capturing region of the first tomographic image; a second tomographic image acquisition unit configured to acquire a second tomographic image of the subject's eye captured at a second time point later than the first time point; a second image capturing region acquisition unit configured to acquire a second image capturing region that is an image capturing region of the second tomographic image; and a display control unit configured to, if one image capturing region of the first image capturing region and the second image capturing region is larger than an other image capturing region that is different from the one image capturing region, perform control to provide, on a display portion, a display of both a tomographic image of only a partial region of the one image capturing region which is a corresponding region corresponding to the other image capturing region and a tomographic image of the other image capturing region.

Furthermore, the present invention includes a control method for the above-described image processing apparatus, and a storage medium storing a program that causes a computer to execute the control method.

Further features of the present invention will become apparent from the following description of exemplary embodiments with reference to the attached drawings.

DESCRIPTION OF THE EMBODIMENTS

Forms (embodiments) for implementing the present invention will be described below with reference to the drawings. In the following embodiments, an example will be described in which an ophthalmological apparatus that captures an image of an eye fundus portion of a subject is applied as an image processing apparatus according to the present invention. Furthermore, in the following embodiments, although an example will be described in which the eye fundus portion of the subject is applied as an object to be examined, the present invention is not limited to this. Any object to be subjected to imaging for a tomographic image, for example, an anterior eye segment, such as a cornea, crystalline lens, or an iris, can be applied.

Figure 1:
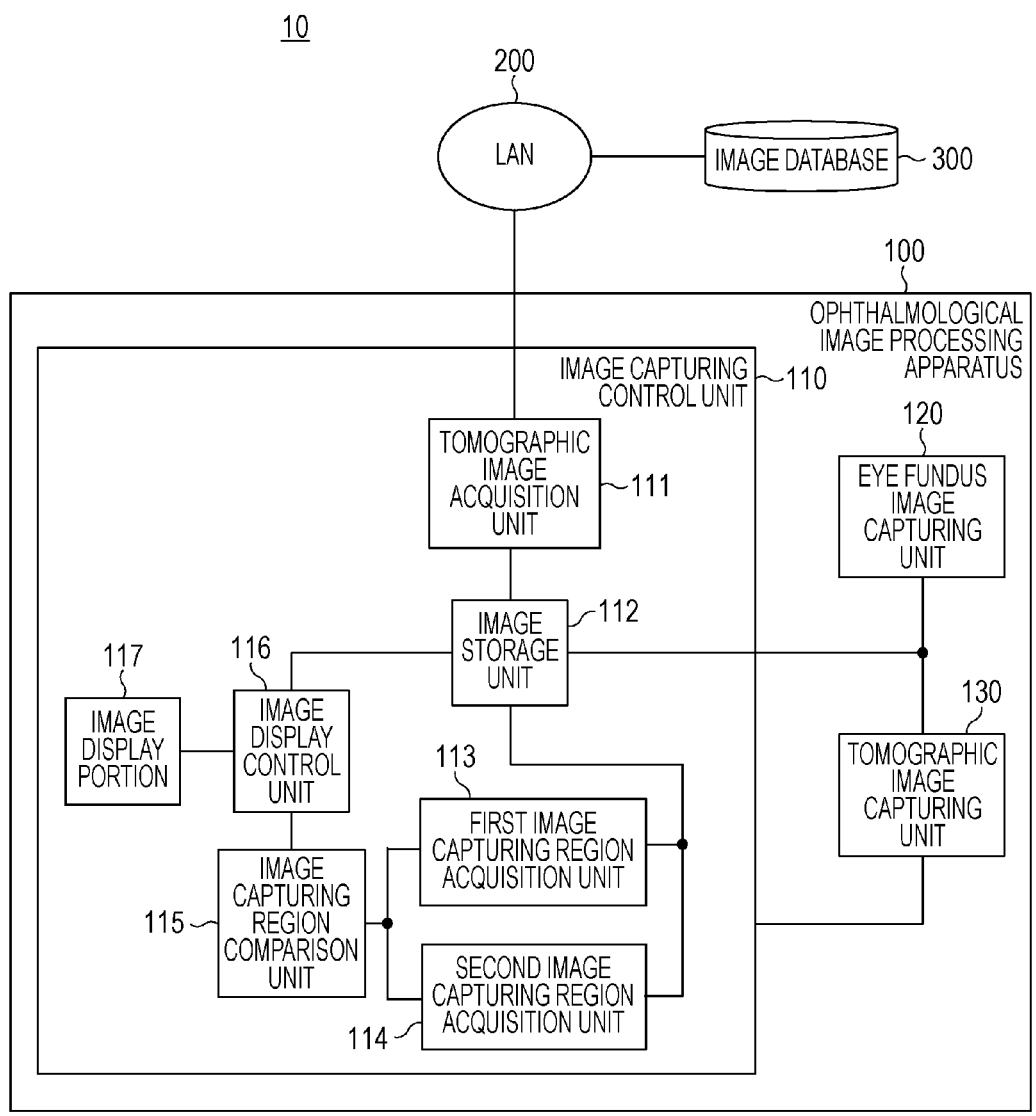
FIG. 1 is a schematic diagram illustrating an example of a schematic configuration of an ophthalmological image processing system according to an embodiment of the present invention.

FIG. 1 is a schematic diagram illustrating an example of a schematic configuration of an ophthalmological image processing system 10 according to an embodiment of the present invention.

As illustrated in FIG. 1, the ophthalmological image processing system 10 includes an ophthalmological image processing apparatus 100, a local area network (LAN) 200, and an image database 300.

The ophthalmological image processing apparatus 100 is connected to the image database 300 that stores an image captured in the past (past image) via the LAN 200. In other words, the ophthalmological image processing apparatus 100 is configured to acquire a past image from the image database 300 and also to store a captured image in the image database 300 as a past image. As illustrated in FIG. 1, this ophthalmological image processing apparatus 100 includes an image capturing control unit 110, an eye fundus image capturing unit 120, and a tomographic image capturing unit 130.

The LAN 200 is a local area network that connects the ophthalmological image processing apparatus 100 to the image database 300 in such a manner that they can communicate with each other.

The image database 300 is a database that stores various types of past images and the like.

Next, an internal configuration of the ophthalmological image processing apparatus 100 will be described.

The image capturing control unit 110 has a function of performing centralized control of operations performed by the ophthalmological image processing apparatus 100 and also a function of processing a captured image or the like. For example, the image capturing control unit 110 controls capturing of an eye fundus image of an eye fundus portion of a subject's eye performed by the eye fundus image capturing unit 120 and also controls capturing of a tomographic image of the eye fundus portion of the subject's eye performed by the tomographic image capturing unit 130.

The eye fundus image capturing unit 120 captures an eye fundus image of the eye fundus portion of the subject's eye on the basis of control performed by the image capturing control unit 110.

The tomographic image capturing unit 130 captures a tomographic image of the eye fundus portion of the subject's eye on the basis of control performed by the image capturing control unit 110.

Furthermore, the eye fundus image capturing unit 120 and the tomographic image capturing unit 130 are connected to each other and are configured so that a tomographic image of an intended region contained in an eye fundus image can be captured while the eye fundus image is being continuously captured. Specifically, a tomographic image of an intended region on an eye fundus image can be captured by controlling a positional relationship between lasers used for capturing of the respective images.

Next, an internal configuration of the image capturing control unit 110 will be described.

As illustrated in FIG. 1, the image capturing control unit 110 includes a tomographic image acquisition unit 111, an image storage unit 112, a first image capturing region acquisition unit 113, a second image capturing region acquisition unit 114, an image capturing region comparison unit 115, an image display control unit 116, and an image display portion 117.

The tomographic image acquisition unit 111 acquires, from the image database 300, as a first tomographic image, a tomographic image of the subject's eye captured at a first time point that is a past time point. Note that, as the first tomographic image, an image captured by, for example, another tomographic image capturing unit other than the tomographic image capturing unit 130 can be used.

The image storage unit 112 stores the first tomographic image or the like acquired by the tomographic image acquisition unit 111 and also stores an eye fundus image captured by the eye fundus image capturing unit 120 and a tomographic image captured by the tomographic image capturing unit 130. Here, a tomographic image that is captured by the tomographic image capturing unit 130 and stored in the image storage unit 112 is a second tomographic image of the same subject's eye captured at a second time point later than the first time point at which the first tomographic image has been captured.

The first image capturing region acquisition unit 113 acquires a first image capturing region that is an image capturing region of the first tomographic image stored in the image storage unit 112. Here, in this embodiment, an aspect can be applied in which the first image capturing region acquisition unit 113 acquires the first image capturing region of the first tomographic image by using, for example, the first tomographic image and an eye fundus image that are stored in the image storage unit 112. Specifically, in the case where this aspect is applied, for example, the first image capturing region acquisition unit 113 aligns an integrated image representing an eye fundus surface with the eye fundus image stored in the image storage unit 112 and thereby acquires the first image capturing region of the first tomographic image on the eye fundus image. The integrated image is generated by performing an averaging process on the first tomographic image in the depth direction. Then, the first image capturing region acquisition unit 113 acquires information, such as the position and size, of the first image capturing region, and outputs this information to the image capturing region comparison unit 115 as first image capturing region information.

The second image capturing region acquisition unit 114 acquires a second image capturing region that is an image capturing region of the second tomographic image stored in the image storage unit 112. Here, in this embodiment, an aspect can be applied in which the second image capturing region acquisition unit 114 acquires the second image capturing region of the second tomographic image by using, for example, the second tomographic image and an eye fundus image that are stored in the image storage unit 112. Specifically, in the case where this aspect is applied, for example, the second image capturing region acquisition unit 114 aligns an integrated image representing an eye fundus surface with the eye fundus image stored in the image storage unit 112 and thereby acquires the second image capturing region of the second tomographic image on the eye fundus image. The integrated image is generated by performing an averaging process on the second tomographic image in the depth direction. Then, the second image capturing region acquisition unit 114 acquires information, such as the position and size, of the second image capturing region, and outputs this information to the image capturing region comparison unit 115 as second image capturing region information.

The image capturing region comparison unit 115 compares the first image capturing region acquired by the first image capturing region acquisition unit 113 with the second image capturing region acquired by the second image capturing region acquisition unit 114. Specifically, the image capturing region comparison unit 115 determines, on the basis of the first image capturing region information (position and size) read from the first image capturing region acquisition unit 113 and the second image capturing region information (position and size) read from the second image capturing region acquisition unit 114, whether one image capturing region of the first image capturing region and the second image capturing region is larger than the other image capturing region that is different from the one image capturing region, or whether the one image capturing region is a region including the other image capturing region.

As a result of a comparison determination made by the image capturing region comparison unit 115, if the above-described one image capturing region is larger than the other image capturing region that is different from the one image capturing region and includes the other image capturing region, the image display control unit 116 performs control to provide, on the image display portion 117, a follow-up display of both a tomographic image of only a partial region of the one image capturing region which is a corresponding region corresponding to the other image capturing region and a tomographic image of the other image capturing region. Specifically, for example, if the above-described one image capturing region is the second image capturing region, and if the above-described other image capturing region is the first image capturing region, the image display control unit 116 performs control to provide, on the image display portion 117, a follow-up display of both the second tomographic image of only a partial region of the second image capturing region which is a corresponding region corresponding to the first image capturing region and the first tomographic image of the first image capturing region. Furthermore, for example, if the above-described one image capturing region is the first image capturing region, and if the above-described other image capturing region is the second image capturing region, the image display control unit 116 performs control to provide, on the image display portion 117, a follow-up display of both the first tomographic image of only a partial region of the first image capturing region which is a corresponding region corresponding to the second image capturing region and the second tomographic image of the second image capturing region. In this way, of the first tomographic image and the second tomographic image, in accordance with the size of the tomographic image whose image capturing region is small, the image display control unit 116 performs control to change a display range of the tomographic image whose image capturing region is large.

The image display portion 117 provides a follow-up display of both the first tomographic image and the second tomographic image on the basis of control performed by the image display control unit 116.

Next, an internal configuration of the tomographic image capturing unit 130 will be described.

Figure 2:
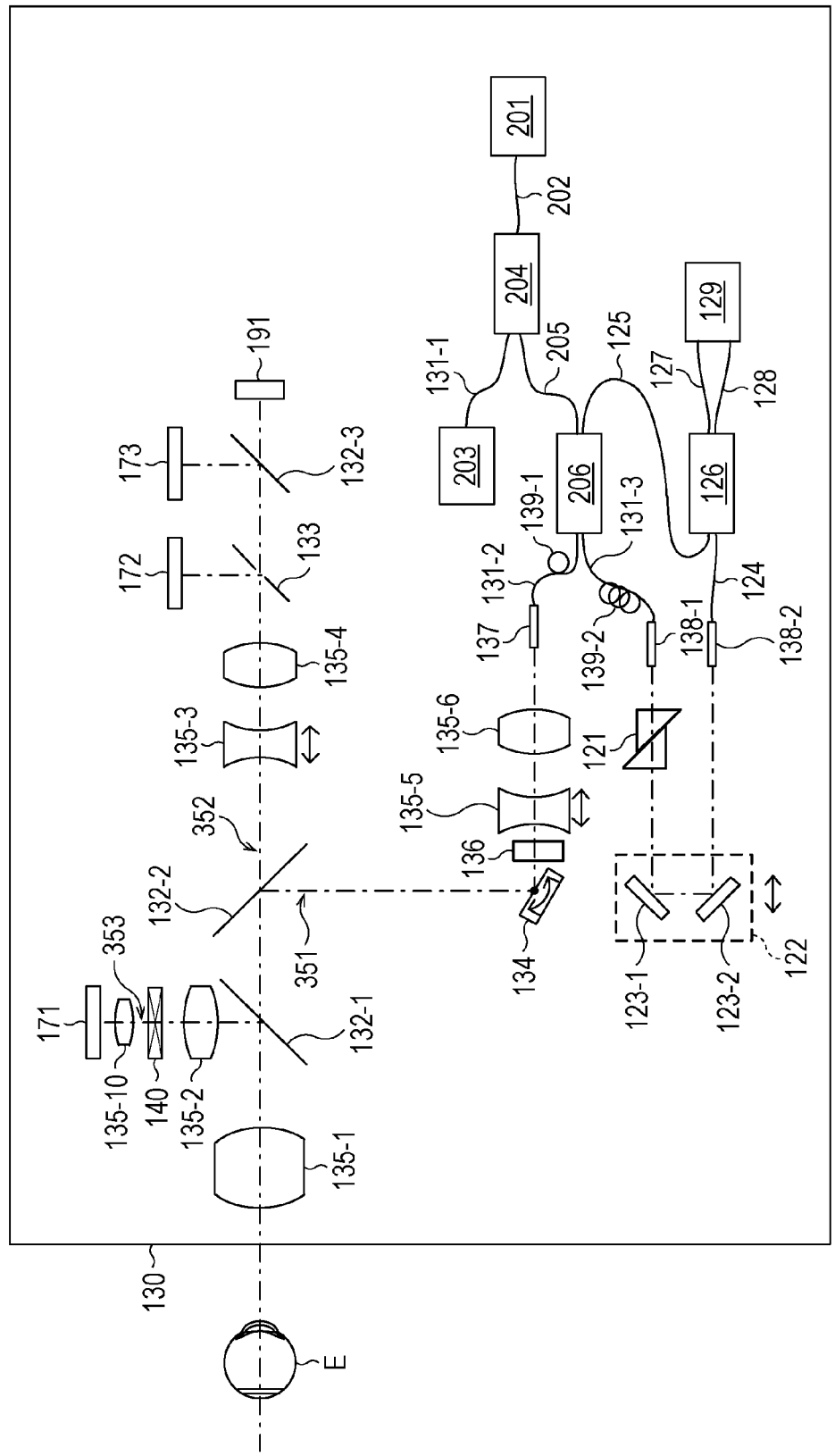
FIG. 2 illustrates an example of an internal configuration of a tomographic image capturing unit illustrated in FIG. 1.

FIG. 2 illustrates an example of an internal configuration of the tomographic image capturing unit 130 illustrated in FIG. 1.

First, a measuring optical system will be described.

An objective lens 135-1 is disposed opposite a subject's eye E. On its optical axis, light is split and directed into an optical path 351 of an optical coherence tomography (OCT) optical system, an optical path 352 for eye fundus observation and a fixation light, and an optical path 353 for anterior eye observation, for respective wavelength bands, by a first dichroic mirror 132-1 and a second dichroic mirror 132-2.

In the optical path 352, light reflected from an eye fundus of the subject's eye E is guided by a perforated mirror 133 to a charge coupled device (CCD) 172 for eye fundus observation. Additionally, to the optical path 352, light from a scanning laser ophthalmoscope (SLO) light source 173 for eye fundus observation and a fixation light 191 is guided by a third dichroic mirror 132-3. Furthermore, in the optical path 352, lenses 135-3 and 135-4 are disposed, and the lens 135-3 is driven by a motor (not illustrated) to perform focusing for the fixation light 191 and eye fundus observation. The SLO light source 173 emits light with a center wavelength of 780 nm. The fixation light 191 generates visible light to prompt eye fixation of the eye of the subject.

In the optical path 353, constituent elements of an optical system for anterior eye observation are disposed from a lens 135-2 to an infrared CCD 171 for anterior eye observation. The constituent elements include a prism 140 and a lens 135-10. The infrared CCD 171 has sensitivity at a wavelength of illumination light for anterior eye observation, specifically, at a wavelength of about 970 nm.

The optical path 351 is an optical path of the OCT optical system as described above and is used for capturing a tomographic image of the eye fundus of the subject's eye E. More specifically, the optical path 351 is an optical path for obtaining an interference signal for generating a tomographic image. In the optical path 351, there are disposed a shutter 136 for applying light to the subject's eye E only during imaging and an XY scanner 134 for scanning the eye fundus of the subject's eye E with light. Although this XY scanner 134 is illustrated as one mirror, the XY scanner 134 performs scanning in two axes directions of X-axis and Y-axis directions. In the optical path 351, lenses 135-5 and 135-6 are further disposed. The lens 135-5 is driven by a motor (not illustrated) to focus light from a light source 201 emitted from a fiber 131-2 connected to a fiber coupler 206 on the eye fundus of the subject's eye E. Through this focusing, light from the eye fundus of the subject's eye E simultaneously forms an image in a spot pattern and enters a leading end of the fiber 131-2.

Next, configurations of an optical path extending from the light source 201 and a reference optical system will be described.

The light source 201 is a wavelength-swept light source capable of varying wavelength and emits light with a center wavelength of about 1040 nm and a bandwidth of about 100 nm, for example. The light emitted from the light source 201 is guided to a fiber coupler 204 via a fiber 202 and is split and directed into a fiber 131-1 for measuring the amount of light and into a fiber 205 for performing OCT measurement. The light emitted from the light source 201 passes through the fiber 131-1 and is measured in terms of the power thereof by a power meter (PM) 203. The light having passed through the fiber 205 is guided to the fiber coupler 206. The fiber coupler 206 functions as a division unit that divides an optical path through which the light from the light source 201 is transmitted into a reference optical path and a measuring optical path. The light from the light source 201 is split into a measuring beam (also referred to as an OCT measuring beam) and a reference beam by the fiber coupler 206. A splitting ratio of the fiber coupler 204 is 99:1, and a splitting ratio of the fiber coupler 206 is 90:10 (reference beam:measuring beam).

The measuring beam split by the fiber coupler 206 is emitted from a fiber leading end 137 via the fiber 131-2. In the fiber 131-2, a measuring beam-side polarization adjustment unit 139-1 is provided. Also, in a fiber 131-3, a reference beam-side polarization adjustment unit 139-2 is provided. These polarization adjustment units have some portions in which a fiber is routed in a loop and can adjust the respective polarization states of the measuring beam and the reference beam by rotating the loop portions on an axis in a longitudinal direction of the fiber to apply a twist to the fiber. In the tomographic image capturing unit 130 in this embodiment, the polarization states of the measuring beam and the reference beam are adjusted and fixed in advance. The emitted measuring beam passes through the measuring optical system and scans a region in an intended range of the eye fundus of the subject's eye E.

The reference beam split by the fiber coupler 206 is emitted from a fiber leading end 138-1 via the fiber 131-3 and the reference beam-side polarization adjustment unit 139-2. The reference beam emitted from the fiber leading end 138-1 passes through dispersion compensation glass 121 and is reflected by reference mirrors 123-1 and 123-2 on a coherence gate stage 122. Subsequently, the reference beam enters a fiber leading end 138-2 and reaches a fiber coupler 126 via a fiber 124.

The coherence gate stage 122 functions as a change unit that changes positions of the reference mirrors 123-1 and 123-2 and adjusts an optical path length of the measuring beam and an optical path length of the reference beam by such a function. The reference mirrors 123-1 and 123-2 are disposed so that a position at which the optical path length of the measuring beam is equal to the optical path length of the reference beam is disposed around the subject. The coherence gate stage 122 is driven by a motor (not illustrated) to respond to a difference or the like in eye axial length of the subject's eye E.

The fiber coupler 126 functions as a combining unit that combines the reference beam having passed through the reference optical path with the measuring beam having passed through the measuring optical path including a fiber 125. Thus, the measuring beam and the reference beam having reached the fiber coupler 126 are combined into interference light. The interference light passes through fibers 127 and 128 and is converted into an electrical signal (interference signal) by a balanced receiver 129 that is a photodetector for detecting combined light. Interference signals output from the balanced receiver 129 are subjected to typical reconstruction processing, and thus a tomographic image is generated and acquired.

Next, a follow-up display, which is one of features of the present invention, will be described with reference to FIGS. 3A to 5.

Figure 3A:
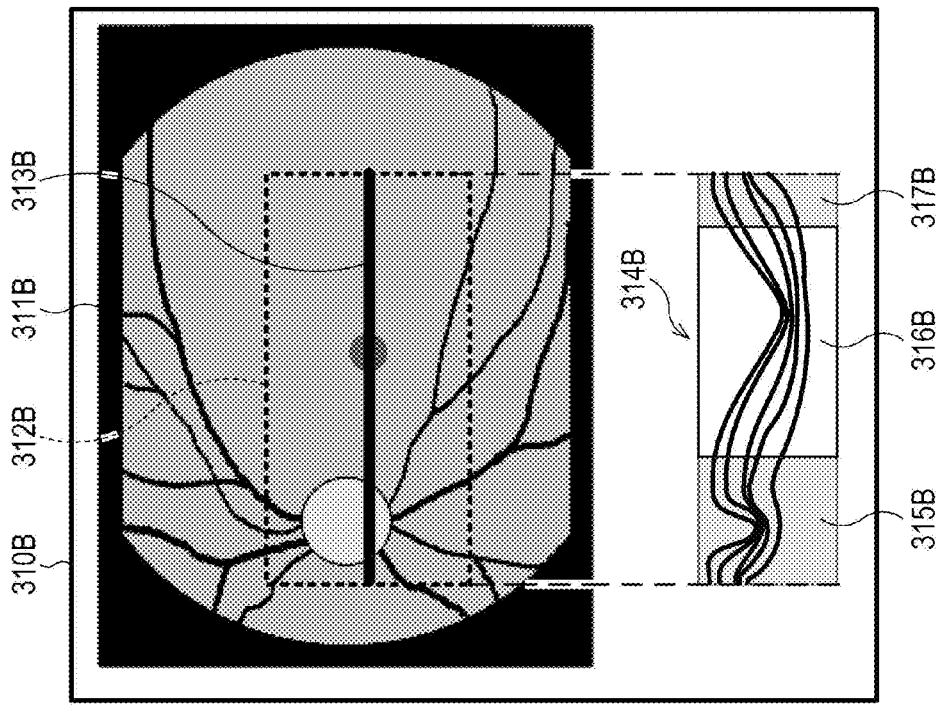
FIGS. 3A and 3B illustrate this embodiment of the present invention and illustrate relationships between tomographic images captured by tomographic image capturing apparatuses with a different size of an image capturing region, and their image capturing ranges.
Figure 3B:
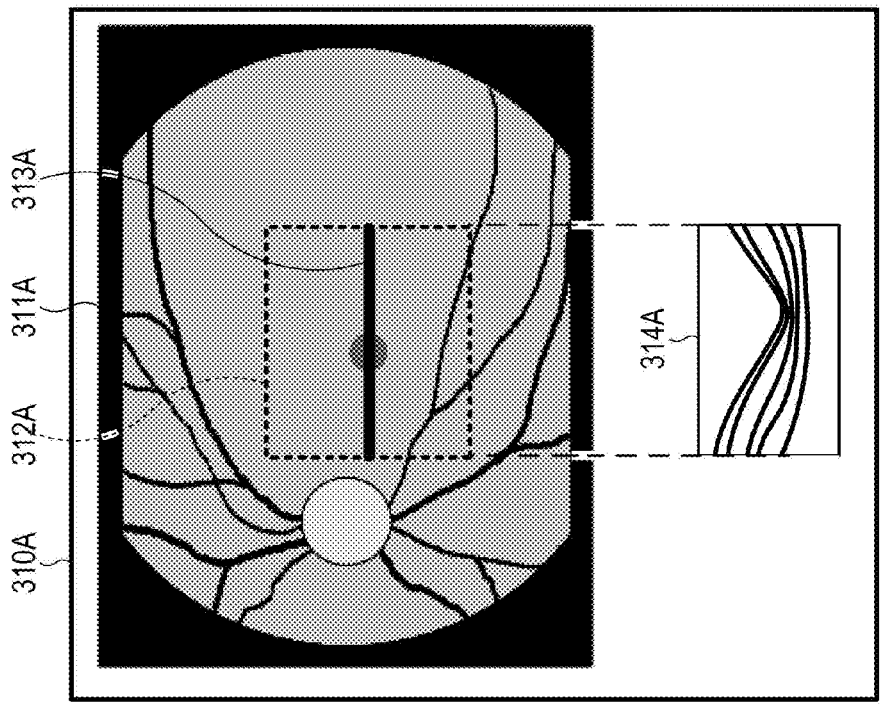

FIGS. 3A and 3B illustrate this embodiment of the present invention and illustrate relationships between tomographic images captured by tomographic image capturing apparatuses with a different size of an image capturing region, and their image capturing ranges.

On a display screen 310A illustrated in FIG. 3A, an eye fundus image 311A, a tomographic image 314A, a tomographic image capturing region 312A, and a position 313A of the tomographic image 314A in the eye fundus image 311A are displayed. Similarly, on a display screen 310B illustrated in FIG. 3B, an eye fundus image 311B, a tomographic image 314B, a tomographic image capturing region 312B, and a position 313B of the tomographic image 314B in the eye fundus image 311B are displayed.

The tomographic image capturing region 312B illustrated in FIG. 3B is larger (wider) than the tomographic image capturing region 312A illustrated in FIG. 3A. Because of this, an image capturing region of the tomographic image 314B illustrated in FIG. 3B is larger (wider) than an image capturing region of the tomographic image 314A illustrated in FIG. 3A.

In the tomographic image 314B illustrated in FIG. 3B, an image region 316B is a corresponding region corresponding to the image capturing region of the tomographic image 314A illustrated in FIG. 3A (that is, the same region as the image capturing region of the tomographic image 314A, of a subject's eye). Furthermore, in the tomographic image 314B illustrated in FIG. 3B, image regions 315B and 317B are non-corresponding regions not corresponding to the image capturing region of the tomographic image 314A illustrated in FIG. 3A (that is, other regions other than the image capturing region of the tomographic image 314A, of the subject's eye). These image regions 315B and 317B are image capturing regions whose tomographic image cannot be acquired in a single imaging session by a tomographic image capturing apparatus that captures the tomographic image 314A illustrated in FIG. 3A.

Figure 4:
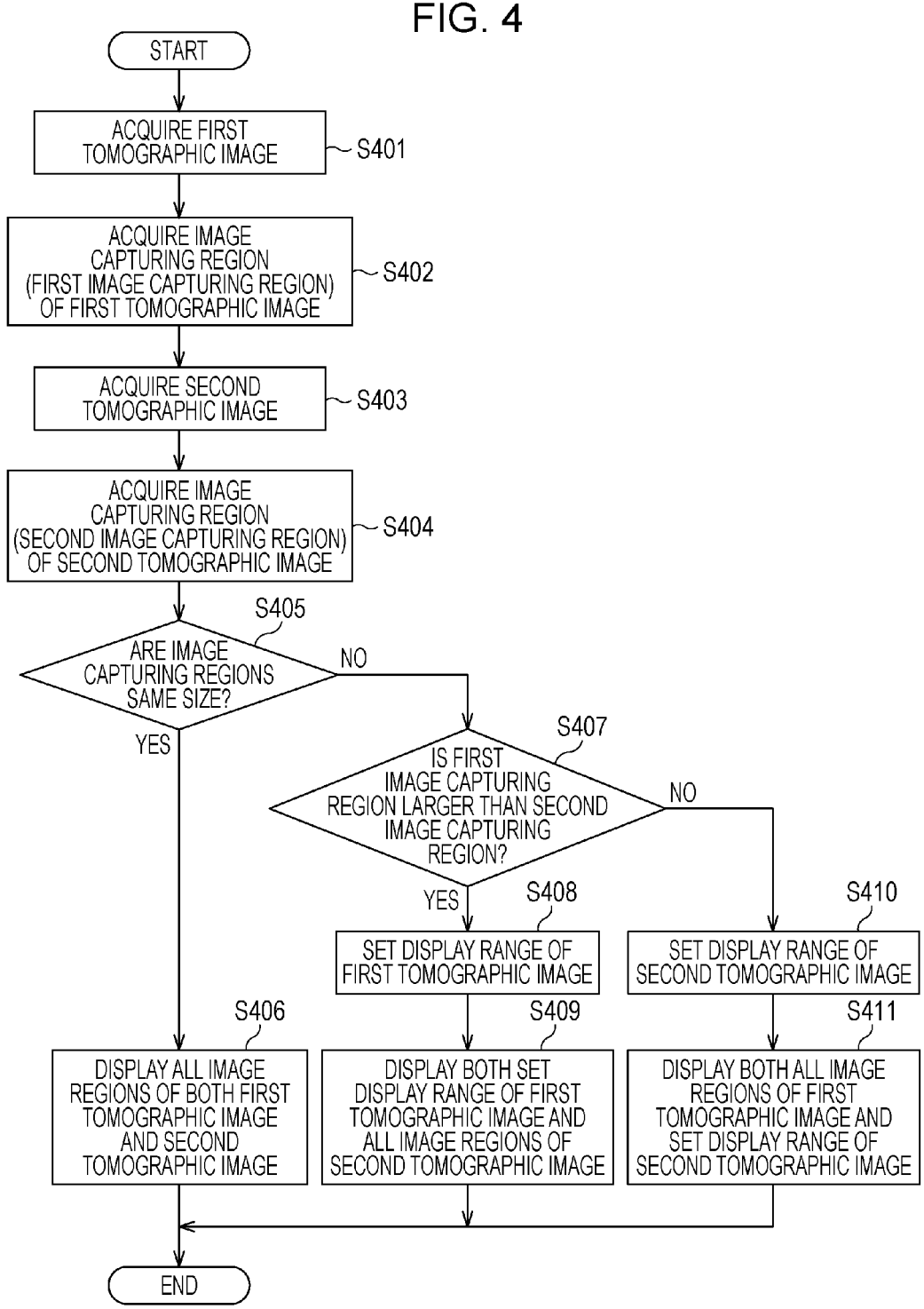
FIG. 4 is a flowchart illustrating an example of a procedure in a control method for an ophthalmological image processing apparatus according to this embodiment of the present invention.

FIG. 4 is a flowchart illustrating an example of a procedure in a control method for the ophthalmological image processing apparatus 100 according to this embodiment of the present invention.

First, in step S401, the tomographic image acquisition unit 111 acquires, from the image database 300 via the LAN 200, as a first tomographic image, a tomographic image of a subject's eye captured at a first time point that is a past time point. The tomographic image acquisition unit 111 that performs this process of step S401 constitutes a first tomographic image acquisition unit. Then, the tomographic image acquisition unit 111 stores the acquired first tomographic image in the image storage unit 112.

Subsequently, in step S402, the first image capturing region acquisition unit 113 acquires a first image capturing region that is an image capturing region of the first tomographic image stored in the image storage unit 112. Here, in this embodiment, an aspect can be applied in which the first image capturing region acquisition unit 113 acquires the first image capturing region of the first tomographic image by using, for example, the first tomographic image acquired in step S401 and stored in the image storage unit 112 and an eye fundus image captured by the eye fundus image capturing unit 120 and stored in the image storage unit 112. Specifically, in the case where this aspect is applied, for example, the first image capturing region acquisition unit 113 aligns an integrated image representing an eye fundus surface with the eye fundus image stored in the image storage unit 112 and thereby acquires the first image capturing region of the first tomographic image on the eye fundus image. The integrated image is generated by performing an averaging process on the first tomographic image in the depth direction. Then, the first image capturing region acquisition unit 113 acquires information, such as the position and size, of the first image capturing region, and outputs this information to the image capturing region comparison unit 115 as first image capturing region information.

Subsequently, in step S403, the tomographic image capturing unit 130 captures, on the basis of control performed by the image capturing control unit 110, a tomographic image of the subject's eye at a second time point later than the first time point at which the first tomographic image has been captured, and acquires this as a second tomographic image. The tomographic image capturing unit 130 that performs this process of step S403 constitutes a second tomographic image acquisition unit. Then, the tomographic image capturing unit 130 stores the acquired second tomographic image in the image storage unit 112.

Subsequently, in step S404, the second image capturing region acquisition unit 114 acquires a second image capturing region that is an image capturing region of the second tomographic image stored in the image storage unit 112. Here, in this embodiment, an aspect can be applied in which the second image capturing region acquisition unit 114 acquires the second image capturing region of the second tomographic image by using, for example, the second tomographic image acquired in step S403 and stored in the image storage unit 112 and an eye fundus image captured by the eye fundus image capturing unit 120 and stored in the image storage unit 112. Specifically, in the case where this aspect is applied, for example, the second image capturing region acquisition unit 114 aligns an integrated image representing an eye fundus surface with the eye fundus image stored in the image storage unit 112 and thereby acquires the second image capturing region of the second tomographic image on the eye fundus image. The integrated image is generated by performing an averaging process on the second tomographic image in the depth direction. Then, the second image capturing region acquisition unit 114 acquires information, such as the position and size, of the second image capturing region, and outputs this information to the image capturing region comparison unit 115 as second image capturing region information.

Subsequently, before the process of step S405 is performed, the image capturing region comparison unit 115 determines, on the basis of the first image capturing region information (position and size) read from the first image capturing region acquisition unit 113 and the second image capturing region information (position and size) read from the second image capturing region acquisition unit 114, whether one image capturing region of the first image capturing region and the second image capturing region is a region including the other image capturing region that is different from the one image capturing region. Then, if the image capturing region comparison unit 115 determines that the above-described one image capturing region is a region including the above-described other image capturing region, the image capturing region comparison unit 115 proceeds to a subsequent step S405. Note that, if the image capturing region comparison unit 115 determines that the above-described one image capturing region is not a region including the above-described other image capturing region, the image capturing region comparison unit 115 does not proceed to the subsequent step S405, and the process of the flowchart in FIG. 4 ends.

In step S405, the image capturing region comparison unit 115 determines, on the basis of the first image capturing region information (position and size) read from the first image capturing region acquisition unit 113 and the second image capturing region information (position and size) read from the second image capturing region acquisition unit 114, whether the above-described one image capturing region is the same size as the above-described other image capturing region. That is, in step S405, it is determined whether the first image capturing region and the second image capturing region are the same size.

As a result of a determination made in step S405, if the above-described one image capturing region is the same size as the above-described other image capturing region (YES in S405), the process flow proceeds to step S406. The case of proceeding to step S406 refers to the case where the first tomographic image and the second tomographic image are tomographic images of the same site of the subject's eye captured at the same size.

In step S406, the image display control unit 116 performs control to provide, on the image display portion 117, a follow-up display of both all image regions of the first tomographic image and all image regions of the second tomographic image.

On the other hand, as a result of a determination made in step S405, if the above-described one image capturing region is not the same size as the above-described other image capturing region (that is, they have a different size) (NO in S405), the process flow proceeds to step S407. The case of proceeding to step S407 refers to the case where the first image capturing region that is an image capturing region of the first tomographic image is different in size from the second image capturing region that is an image capturing region of the second tomographic image.

In step S407, the image capturing region comparison unit 115 determines whether the first image capturing region acquired by the first image capturing region acquisition unit 113 is larger than the second image capturing region acquired by the second image capturing region acquisition unit 114.

As a result of a determination made in step S407, if the first image capturing region acquired by the first image capturing region acquisition unit 113 is larger than the second image capturing region acquired by the second image capturing region acquisition unit 114 (YES in S407), the process flow proceeds to step S408.

In step S408, for example, the image display control unit 116 detects a corresponding region corresponding to the second image capturing region of the second tomographic image from within the first image capturing region of the first tomographic image and sets the corresponding region as a display range of the first tomographic image. That is, the display range of the first tomographic image is set so as to be the same region as the second image capturing region of the second tomographic image whose image capturing region is small.

Subsequently, in step S409, the image display control unit 116 performs control to provide, on the image display portion 117, a follow-up display of both the display range set in step S408 of the first tomographic image and all image regions of the second tomographic image.

On the other hand, as a result of a determination made in step S407, if the first image capturing region acquired by the first image capturing region acquisition unit 113 is not larger than (that is, is smaller than) the second image capturing region acquired by the second image capturing region acquisition unit 114 (NO in S407), the process flow proceeds to step S410.

In step S410, for example, the image display control unit 116 detects a corresponding region corresponding to the first image capturing region of the first tomographic image from within the second image capturing region of the second tomographic image and sets the corresponding region as a display range of the second tomographic image. That is, the display range of the second tomographic image is set so as to be the same region as the first image capturing region of the first tomographic image whose image capturing region is small.

Subsequently, in step S411, the image display control unit 116 performs control to provide, on the image display portion 117, a follow-up display of both all image regions of the first tomographic image and the display range set in step S410 of the second tomographic image.

If the process of step S406, the process of step S409, or the process of step S411 is completed, the process of the flowchart illustrated in FIG. 4 ends.

Figure 5:
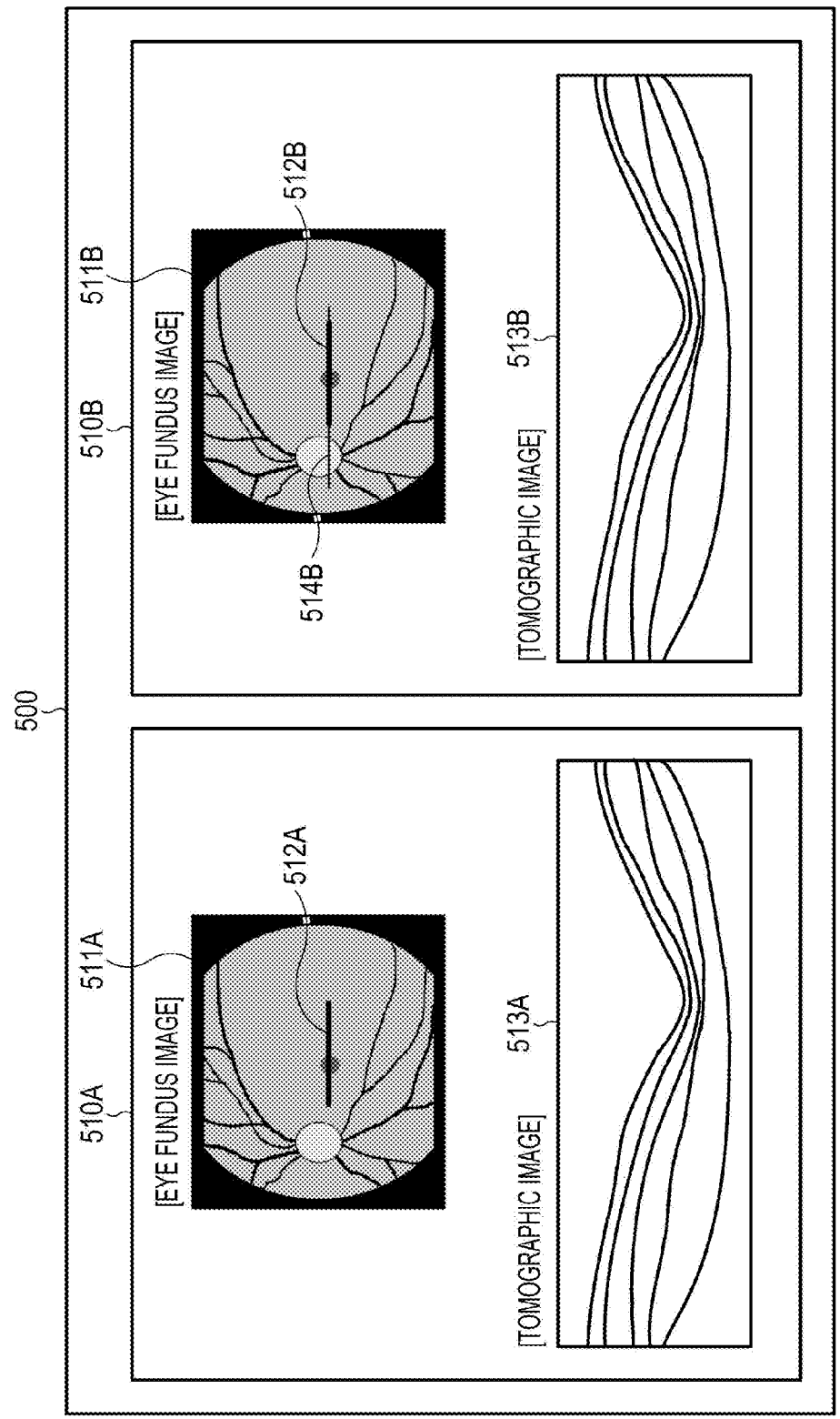
FIG. 5 illustrates this embodiment of the present invention and illustrates an example of a follow-up display in which tomographic images whose image capturing regions have a different size are used.

FIG. 5 illustrates this embodiment of the present invention and illustrates an example of a follow-up display in which tomographic images whose image capturing regions have a different size are used. On a follow-up display screen 500 illustrated in FIG. 5, there are displayed an image display region 510A displaying, for example, a tomographic image captured by a tomographic image capturing apparatus in which an image capturing region is narrow, and an image display region 510B displaying, for example, a tomographic image captured by a tomographic image capturing apparatus in which an image capturing region is wide.

In the image display region 510A, an eye fundus image 511A and a tomographic image 513A are displayed. Furthermore, in the eye fundus image 511A, a position 512A of the tomographic image 513A in the eye fundus image 511A is displayed.

In the image display region 510B, an eye fundus image 511B and a position 514B of a tomographic image acquired by the tomographic image capturing apparatus in the eye fundus image 511B are displayed. Also, a tomographic image of a partial region of the tomographic image acquired by the tomographic image capturing apparatus is displayed as a tomographic image 513B. The partial region is a corresponding region corresponding to an image capturing region of the tomographic image 513A. Furthermore, in the eye fundus image 511B, a position 512B of the displayed tomographic image 513B of the tomographic image acquired by the tomographic image capturing apparatus in the eye fundus image 511B is displayed.

In the example illustrated in FIG. 5, all image regions of the tomographic image captured by the tomographic image capturing apparatus in which an image capturing region is narrow are displayed as the tomographic image 513A. A partial region of the tomographic image captured by the tomographic image capturing apparatus in which an image capturing region is wide is displayed as the tomographic image 513B. The partial region is the corresponding region corresponding to the image capturing region of the tomographic image 513A. As described above, in a follow-up display in which tomographic images whose image capturing regions have a different size are used, as for a tomographic image captured by a tomographic image capturing apparatus in which an image capturing region is wide, only a region corresponding to a tomographic image captured by a tomographic image capturing apparatus in which an image capturing region is narrow is displayed, and thus a follow-up display of only corresponding regions of two tomographic images compared with each other can be provided without changing scaling factors of the two tomographic images, enabling accurate and easy follow-up observation of a subject's eye.

That is, according to this embodiment, even in the case where follow-up observation of the subject's eye is carried out using tomographic images whose image capturing regions have a different size, a comparative understanding of corresponding portions between the tomographic images can be facilitated, thereby enabling a reduction in the burden of follow-up observation on an examiner.

Other Embodiments

In the above-described embodiment of the present invention, although the example is described in which a tomographic image captured by the tomographic image capturing unit 130 is used as the second tomographic image in step S403 in FIG. 4, the present invention is not limited to this form. For example, the following form is applicable to the present invention. In the form, the tomographic image acquisition unit 111 acquires, as the second tomographic image, a tomographic image captured at a second time point later than a first time point at which the first tomographic image acquired in step S401 has been captured, from the image database 300. In the case of this form, the tomographic image acquisition unit 111 that acquires the second tomographic image constitutes the second tomographic image acquisition unit.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-126044, filed Jun. 23, 2015, which is hereby incorporated by reference herein in its entirety.

What is claimed is:

1. An image processing apparatus comprising:
    a first tomographic image acquisition unit configured to acquire a first tomographic image of a subject's eye captured at a first time point that is a past time point;
    a first image capturing region acquisition unit configured to acquire a first image capturing region that is an image capturing region of the first tomographic image;
    a second tomographic image acquisition unit configured to acquire a second tomographic image of the subject's eye captured at a second time point later than the first time point;
    a second image capturing region acquisition unit configured to acquire a second image capturing region that is an image capturing region of the second tomographic image; and
    a display control unit configured to, if one image capturing region of the first image capturing region and the second image capturing region is larger than an other image capturing region that is different from the one image capturing region, perform control to provide, on a display portion, a display of both a tomographic image of only a partial region of the one image capturing region which is a corresponding region corresponding to the other image capturing region and a tomographic image of the other image capturing region.

2. The image processing apparatus according to claim 1, wherein, if the one image capturing region is larger than the other image capturing region and includes the other image capturing region, the display control unit performs the control to provide the display.

3. The image processing apparatus according to claim 2, wherein, if the one image capturing region is the second image capturing region, and if the other image capturing region is the first image capturing region, the display control unit performs control to provide, on the display portion, a display of both the second tomographic image of only a partial region of the second image capturing region which is a corresponding region corresponding to the first image capturing region and the first tomographic image of the first image capturing region.

4. The image processing apparatus according to claim 2, wherein, if the one image capturing region is the first image capturing region, and if the other image capturing region is the second image capturing region, the display control unit performs control to provide, on the display portion, a display of both the first tomographic image of only a partial region of the first image capturing region which is a corresponding region corresponding to the second image capturing region and the second tomographic image of the second image capturing region.

5. The image processing apparatus according to claim 1, wherein, if the one image capturing region is the second image capturing region, and if the other image capturing region is the first image capturing region, the display control unit performs control to provide, on the display portion, a display of both the second tomographic image of only a partial region of the second image capturing region which is a corresponding region corresponding to the first image capturing region and the first tomographic image of the first image capturing region.

6. The image processing apparatus according to claim 1, wherein, if the one image capturing region is the first image capturing region, and if the other image capturing region is the second image capturing region, the display control unit performs control to provide, on the display portion, a display of both the first tomographic image of only a partial region of the first image capturing region which is a corresponding region corresponding to the second image capturing region and the second tomographic image of the second image capturing region.

7. A control method for an image processing apparatus, the control method comprising:
    a first tomographic image acquisition step of acquiring a first tomographic image of a subject's eye captured at a first time point that is a past time point;
    a first image capturing region acquisition step of acquiring a first image capturing region that is an image capturing region of the first tomographic image;
    a second tomographic image acquisition step of acquiring a second tomographic image of the subject's eye captured at a second time point later than the first time point;
    a second image capturing region acquisition step of acquiring a second image capturing region that is an image capturing region of the second tomographic image; and
    a display control step of, if one image capturing region of the first image capturing region and the second image capturing region is larger than an other image capturing region that is different from the one image capturing region, performing control to provide, on a display portion, a display of both a tomographic image of only a partial region of the one image capturing region which is a corresponding region corresponding to the other image capturing region and a tomographic image of the other image capturing region.

8. The control method for the image processing apparatus according to claim 7, wherein, in the display control step, if the one image capturing region is larger than the other image capturing region and includes the other image capturing region, the control is performed to provide the display.

9. The control method for the image processing apparatus according to claim 8, wherein, in the display control step, if the one image capturing region is the second image capturing region, and if the other image capturing region is the first image capturing region, control is performed to provide, on the display portion, a display of both the second tomographic image of only a partial region of the second image capturing region which is a corresponding region corresponding to the first image capturing region and the first tomographic image of the first image capturing region.

10. The control method for the image processing apparatus according to claim 8, wherein, in the display control step, if the one image capturing region is the first image capturing region, and if the other image capturing region is the second image capturing region, control is performed to provide, on the display portion, a display of both the first tomographic image of only a partial region of the first image capturing region which is a corresponding region corresponding to the second image capturing region and the second tomographic image of the second image capturing region.

11. The control method for the image processing apparatus according to claim 7, wherein, in the display control step, if the one image capturing region is the second image capturing region, and if the other image capturing region is the first image capturing region, control is performed to provide, on the display portion, a display of both the second tomographic image of only a partial region of the second image capturing region which is a corresponding region corresponding to the first image capturing region and the first tomographic image of the first image capturing region.

12. The control method for the image processing apparatus according to claim 7, wherein, in the display control step, if the one image capturing region is the first image capturing region, and if the other image capturing region is the second image capturing region, control is performed to provide, on the display portion, a display of both the first tomographic image of only a partial region of the first image capturing region which is a corresponding region corresponding to the second image capturing region and the second tomographic image of the second image capturing region.

13. A storage medium storing, in a non-transitory manner, a program that causes a computer to execute each step of the control method for the image processing apparatus according to claim 7.

* * * * *